United States Patent
Maeda et al.

(10) Patent No.: US 7,456,951 B2
(45) Date of Patent: Nov. 25, 2008

(54) FLUORESCENCE DETECTION METHOD, DETECTION APPARATUS AND FLUORESCENCE DETECTION PROGRAM

(75) Inventors: Koshi Maeda, Hitachinaka (JP); Shinichi Fukuzono, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 228 days.

(21) Appl. No.: 11/285,146

(22) Filed: Nov. 23, 2005

(65) Prior Publication Data
US 2006/0109460 A1    May 25, 2006

(30) Foreign Application Priority Data
Nov. 25, 2004   (JP)   ............... 2004-339917

(51) Int. Cl.
*G01J 3/30* (2006.01)
(52) U.S. Cl. .................................... 356/317
(58) Field of Classification Search ......... 356/317–318, 356/417; 250/458.1
See application file for complete search history.

(56) References Cited

U.S. PATENT DOCUMENTS

| | | | | |
|---|---|---|---|---|
| 6,160,618 A | * | 12/2000 | Garner | ........................ 356/318 |
| 7,057,185 B2 | * | 6/2006 | Curry et al. | ............... 250/459.1 |
| 2003/0016352 A1 | * | 1/2003 | Goldman et al. | ............. 356/317 |
| 2003/0020908 A1 | * | 1/2003 | Frost et al. | ................... 356/317 |
| 2003/0160184 A1 | * | 8/2003 | Curry et al. | ............... 250/459.1 |
| 2005/0228231 A1 | * | 10/2005 | MacKinnon et al. | ........ 600/178 |

FOREIGN PATENT DOCUMENTS

JP    58-021143    2/1983

* cited by examiner

*Primary Examiner*—Kara E Geisel
(74) *Attorney, Agent, or Firm*—McDermott Will & Emery LLP (57) ABSTRACT

In fluorescence detection, complicated concentration adjustment and retry of detection operation can be eliminated. In a fluorescence detection method for irradiating an exciting light ray on a fluorescent material or a sample having the fluorescent material to detect fluorescent luminescent rays emanated under the irradiation, the fluorescent luminescence rays parameterized by a plurality of wavelengths in a wavelength band of a fluorescent area are detected simultaneously, wavelengths which parameterize fluorescence intensities detected within a detection range are adopted from the plurality of wavelengths and the fluorescence intensities parameterized by the adopted wavelengths are delivered as detection results. The present invention also discloses a fluorescence detection apparatus and a program for a computer.

6 Claims, 8 Drawing Sheets

FLUORESCENCE DETECTION METHOD, DETECTION APPARATUS AND FLUORESCENCE DETECTION PROGRAM

BACKGROUND OF THE INVENTION

The present invention relates to fluorescence detection method, detection apparatus and fluorescence detection program and more particularly, to a technology for automating fluorescence photometric method and fluorescence photometric apparatus.

In a conventional fluorescence detection apparatus, a sample labeled with a fluorescent material is irradiated with an exciting light ray of an excitation wavelength optimized for the labeled fluorescent material and a fluorescent luminescence ray associated with a wavelength, at which the highest fluorescence intensity is exhibited in a wavelength band of a luminescence area characteristic of the labeled fluorescent material, is detected to quantitatively determine the sample. When detecting an unknown fluorescent material within a detection range of fluorescent analyzer, a method as disclosed in JP-A-58-21143 (Patent Document) is available according to which an analysis is made within a detectable range by changing the sensitivity of an amplifier.

Figure 11:
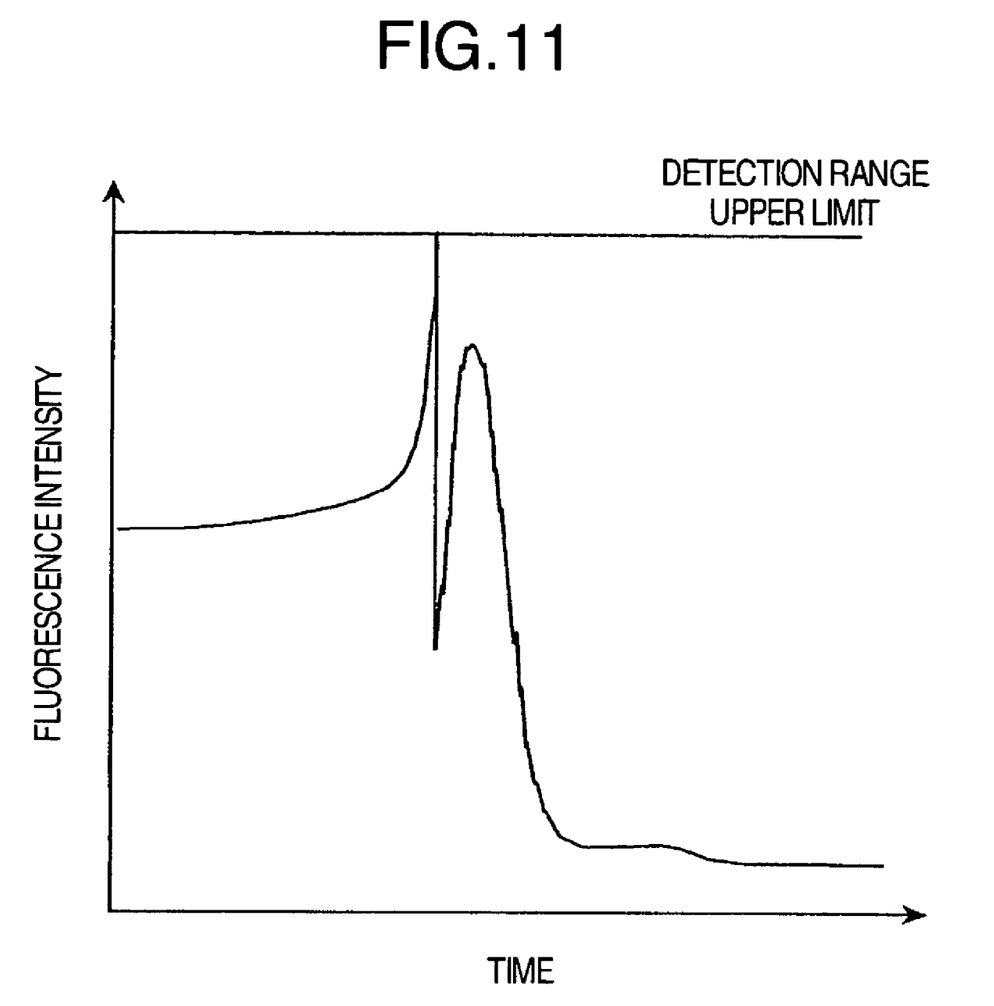
FIG. 11 is a graphical representation showing a fluorescence intensity output obtained when the sensitivity of an amplifier is changed pursuant to the conventional technique disclosed in the previously-described Patent Document.

In carrying out fluorescence detection in respect of a fluorescent material having an unknown concentration or a sample labeled with the fluorescent material having an unknown concentration, the wavelength band of exciting light wavelengths or the sensitivity of an amplifier is changed as indicated in the Patent Document, or alternatively the concentration of the sample is measured and the sample is diluted or enriched in accordance with a measured concentration, thereby assuring detection within the detection range. With the sensitivity of the amplifier changed for the sake of confining detection intensities in the detection range, there arises a problem that the detection waveform is distorted as shown in FIG. 11 or the difference in detection sensitivity occurs between a standard sample and the sample to be inspected (inspection sample). For example, in determining a concentration of the inspection sample in terms of a relative value to that of the standard sample from an area of a detected waveform, difficulties are encountered in accurately settling the detected waveform area. Further, in setting up a base line (background) during determination of a concentration of the inspection sample and a relative value thereof to that of the standard sample, the positioning of a base line by drawing the line from start point to end point for an detected waveform is difficult due to the method that as the amplification sensitivity is switched from one level to another, the start point or end point of detection value changes before and after its switch.

Further, for adjustment of the concentration of a sample, processing procedures are needed including the steps of detecting a concentration of the sample and adjusting the concentration of the sample as well as adjusting again the concentration of a sample which is determined, after detection, as deviating from the detection range, thus being considered to be problematic from the standpoints of the complexity of operation and the throughput. In addition, in the case of an apparatus for detecting many samples of different concentrations, different concentration adjustment operations are necessary for a host of samples and the operations can be automated only at the cost of the provision of a mechanism having a system for detecting concentrations, a pipetting device capable of adjusting individual samples separately and a space made room for dilution and enrichment, causing many problems leading to high costs, degraded throughput and augmented scale for the automated pipetting device.

SUMMARY OF THE INVENTION

According to the present invention, in a fluorescence detection method for irradiating an exciting light ray onto a fluorescent material or a sample labeled with the fluorescent material to detect fluorescent luminescence rays generated under the irradiation. The fluorescent luminance rays of a number of different intensity can be simultaneously detected by using to detect a plurality of wavelengths in a fluorescent wavelength band of a fluorescent material, wavelengths which parameterize fluorescence intensities detected within a detection range are adopted selectively from the plurality of wavelengths, and the fluorescence intensities parameterized by the adopted wavelengths are outputted as detection results. In the above method, in so far as the detection results include fluorescence wavelengths which parameterize fluorescence intensities outside the detection range, these fluorescence wavelengths are excluded and the remaining fluorescence wavelengths are adopted, so that fluorescence intensities parameterized by the adopted wavelengths can be delivered as detection results. A wavelength, which parameterizes the maximum fluorescence intensity within the detection range, can be an adoptable wavelength. However, the adoptable wavelength may not be limited to the one by which the maximum fluorescence intensity is parameterized but may be a wavelength which parameterizes an arbitrary intensity within the detection range.

Also according to the present invention, in a fluorescence detection method for irradiating an exciting light ray onto a plurality of kinds of fluorescent materials or samples labeled the fluorescent materials to detect fluorescent luminescence rays generated under the irradiation, the fluorescent luminescence rays parameterized by a plurality of wavelengths in wavelength bands of luminescent areas are detected simultaneously, wavelengths which parameterize fluorescence intensities detected within a detection range are adopted selectively from the plurality of wavelengths, and the fluorescence intensities parameterized by the adopted wavelengths are outputted as detection results. In the above method, in so far as the detection results include fluorescence wavelengths which parameterize fluorescence intensities outside the detection range, these fluorescence wavelengths are excluded and the remaining fluorescence wavelengths are adopted, so that fluorescence intensities parameterized by the adopted wavelengths can be delivered as detection results. The adoptable fluorescence wavelength may differ with the individual fluorescent materials. In addition, the present invention provides computer program and fluorescence detection apparatus useful for the detection methods as above.

According to the present invention, preparation for a sample, for example, concentration adjustment can be omitted or simplified and therefore, an intended detection signal can be acquired easily and accurately without increasing the number of detection operations. Accordingly, according to this invention, various kinds of fluorescence detection techniques, for instance, can be automated.

This invention targets techniques for detection of fluorescent luminescence rays such as employed in, for example, a DNA sequencer, a liquid chromatography apparatus and a spectrometer. In the fluorescence detection, any detector has an upper limit of detection range, with the result that in the case of measurement of fluorescence intensities a highly concentrated fluorescent material or a sample labeled with the fluorescent material exhibits, a detected fluorescence intensity exceeds the detection range, thereby making it necessary to perform either readjustment for confining the concentration in the detection range or pre-adjustment for confining the concentration in the detection range and eventually raising a problem that the operation is complicated. In addition, in the case of an apparatus for detecting many samples of different concentrations, different concentration adjustment operations are required for hosts of samples and inasmuch as the apparatus is automated, there arise problems leading to increased apparatus cost, degraded throughput and augmented scale. Further, in the method of the aforementioned Patent Document, the sensitivity of the amplifier is switched and consequently, in determining the fluorescence intensity and the area of a detected peak, the accuracy will be degraded disadvantageously.

In the present invention, by making use of a phenomenon that fluorescent luminescence rays generated under irradiation of an exciting light ray onto a fluorescent material exhibit different fluorescence intensities parameterized by different wavelengths for detection in a luminescent area characteristic of the fluorescent material, the fluorescent luminescence rays parameterized by a plurality of wavelengths in the overall luminescent area characteristic of the fluorescent material are detected simultaneously and wavelengths which parameterize fluorescence intensities detected within the detection range, preferably, a wavelength which parameterizes the highest fluorescence intensity is adopted, thereby ensuring that samples of any different concentrations can be detected within the detection range without resort to the concentration adjustment.

According to the invention, in a method of detecting fluorescence intensities of fluorescent luminescence rays excited from fluorescent materials, fluorescent materials having any concentrations can be detected within a detection range. Results of study have demonstrated that even when the concentration differs greatly showing a ratio of minimum to maximum of 1:20, the fluorescence intensity can be procured within the detection range by selecting detection wavelengths. Particularly, in a method for performing quantitative relative measurement of fluorescent materials or a plurality of samples labeled with the fluorescent materials, fluorescence intensities or fluorescent waveform areas can be measured with high accuracies in respect of samples of any concentration levels and concentrations of the samples can be settled.

Further, in automating the fluorescence detection, a step of detecting a concentration of a sample, a step of adjusting the concentration of the sample and a step of readjusting the concentration of a sample deviating from the detection range as well can be omitted to detect the sample within the detection range. Through this, many samples of different concentrations can be treated through a routine process and in automating the apparatus, the mechanism including a system for detecting concentration, an apportioning system capable of adjusting individual samples separately and a space necessary for dilution and enrichment can be omitted, thereby realizing cost reduction of the apparatus, augmented throughput and scale reduction.

The lower the fluorescence intensity detected from a measuring object, the lower the S/N (signal-to-noise) ratio relative to the baseline becomes, making accurate detection of fluorescence intensity difficult but in the present invention, by selecting the maximum fluorescence intensity within the detection range, the sample can always be detected with the maximum sensitivity and analysis or detection with high S/N ratio accuracy can be assured.

Other objects, features and advantages of the invention will become apparent from the following description of the embodiments of the invention taken in conjunction with the accompanying drawings.

DESCRIPTION OF THE EMBODIMENTS

The above and other novel features and advantages of the present invention will be described specifically hereunder with reference to the accompanying drawings. The present invention provides fluorescence detection method and apparatus in which an exciting light ray optimized for excitation of a fluorescent material or a sample labeled with the fluorescent material is irradiated onto the sample, fluorescent luminescence rays emanated from the fluorescent material under the irradiation and parameterized by a plurality of wavelengths are measured simultaneously, and fluorescence intensities parameterized by wavelengths and detected within a detection range are delivered as detection results.

Figure 3:
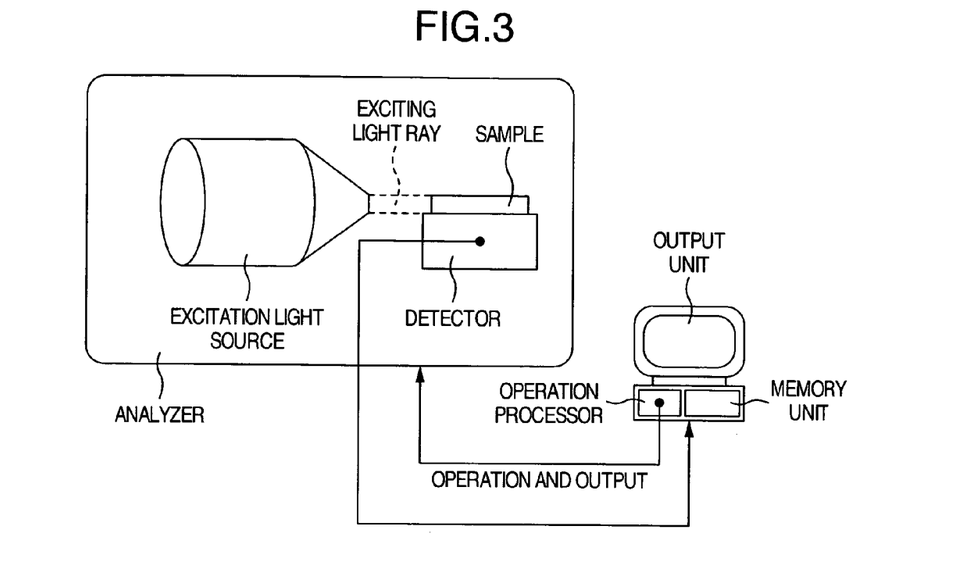
FIG. 3 is a schematic diagram showing the construction of a detection apparatus to which the present invention is applied.

A system according to the present invention is configured as schematically illustrated in FIG. 3. The system comprises, at least, a light source for exciting a fluorescent material or a sample labeled with the fluorescent material, a detector capable of performing simultaneous photometry of excited fluorescent luminescence rays parameterized by a plurality of wavelengths, a memory unit capable of saving individual fluorescence intensities parameterized by the plurality of wavelengths, a program for selecting fluorescence intensities within a detection range from the stored fluorescence intensities, and an output unit for displaying the selected fluorescence intensities. These components are related together as exemplified in FIGS. 4A and 4B. In these examples, an exciting light ray from an excitation light source 1 is irradiated onto a sample labeled with a fluorescent material 2, fluorescence intensities parameterized by a plurality of wavelengths are detected by using a detector 3 capable of performing simultaneous photometry of fluorescent luminescence rays parameterized by a band of plural wavelengths, the fluorescence intensities are stored in a memory unit 4, a fluorescence intensity parameterized by an optimum wavelength is selected by means of an operation processor 5, and the selected fluorescence intensity is delivered to an output unit 6. Obviously, the operation processor 5 also includes a temporary memory device. In essentiality, the present system may comprise the detector for performing simultaneous photometry of fluorescent luminescence rays parameterized by a plurality of wavelengths and the program for selecting fluorescence intensities within the detection range from the fluorescence intensities parameterized by the plural wavelengths and obtained from the detector and therefore, the system configuration is in no way limited to the above examples.

The program used in the present invention includes a fluorescence detection program for causing a computer, which performs operation of outputs from the fluorescence detection apparatus, to function as means for setting a plurality of detection wavelengths in the fluorescence detector, means for irradiating an exciting light ray onto a fluorescent material or a sample labeled with the fluorescent material, means for detecting fluorescent luminescence rays emitted from the excited fluorescent material, means for deciding whether detected fluorescence intensities include those outside a detection range, and means for performing operation, when the fluorescence intensities outside the detection range are included, by using a plurality of fluorescence intensities confined in the detection range while excluding the fluorescence intensities outside the detection range or means for selecting, when fluorescence intensities outside the detection range are not included, the maximum fluorescence intensity from the plural fluorescence intensities within the detection range. More specifically, the above program can be applicable to the case where an exciting light ray is irradiated onto plural kinds of fluorescent materials or samples having the plural fluorescent materials.

For example, as the fluorescent material to be detected or the fluorescent material labeled to the sample, fluorescein isothiocyanate (FITC), tetramethyl rhodamine isothiocyanate (TRITC) or quantum dots representing a composite of metal compound and organic compound capable of luminescing fluorescence with various kinds of light sources but any material may be used provided that it can emanate a fluorescent luminescence ray under irradiation of an optimum exciting light ray.

For example, as the excitation light source, an argon ion laser, a helium-neon ion laser and a semiconductor laser may be enumerated but any light source may be used provided that it can permit acquisition of an intended fluorescent luminescence ray from the fluorescent material. Preferably, a light source optimized for enabling the detection fluorescent material to luminesce.

For example, as the detector capable of simultaneously measuring the overall luminescence area of fluorescent luminescence rays which are emanated from a fluorescent material excited by the excitation light source and which are parameterized by a plurality of wavelengths, a CCD representing semiconductor sensor and a detector having arrayed photodiodes or alternatively, a detector for performing spectroscopy by using a prism or grating and detecting spectra by means of a photodetector, an excitation spectroscope and a fluorescence spectrometer can be enumerated but it suffices that, in the present system, excited fluorescent luminescence rays parameterized by a plurality of wavelengths be detected simultaneously and the example as above is not limitative.

Figure 5:
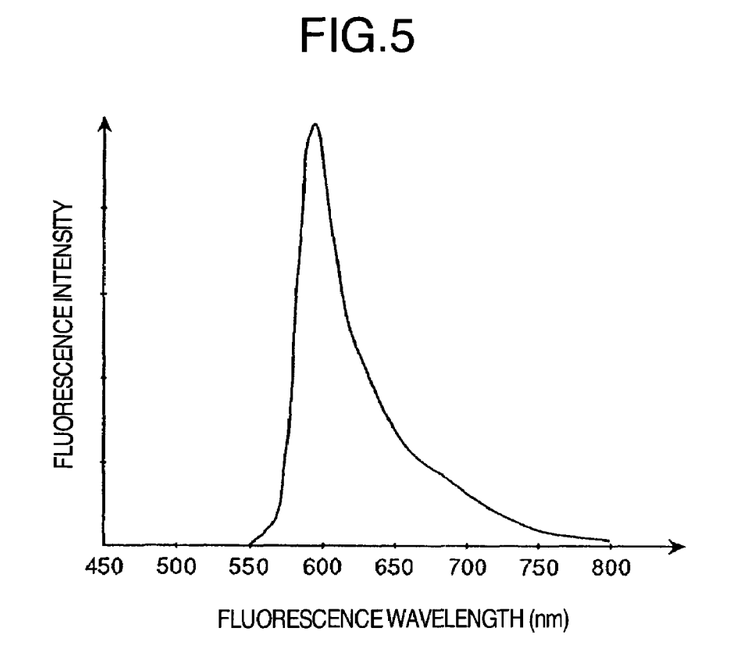
FIG. 5 is a graph showing a common fluorescent luminescence spectrum of a fluorescent material having an excitation wavelength at 600 nm.

When detecting the overall luminescent area of fluorescent luminescence rays parameterized by a plurality of wavelengths simultaneously by using the aforementioned detector, it is preferable that the sensitivity of the detector be set to the maximum sensitivity in a set range in order for the detector to be able to detect even a small amount. For detection, any wavelengths can be used on condition that wavelengths used are two or more in number. Generally speaking, however, a fluorescent luminescence spectrum has the property exhibiting a steep gradient during rising and an easy gradient during attenuation as shown in FIG. 5 and preferably, for use in detection, not only a wavelength optimized for the fluorescent material but also a longer wavelength than the optimized one may be set. More specifically, it is preferable that for the sake of performing detection with high S/N ratio regardless of the level of fluorescence intensity of a detection peak, five kinds of wavelengths be set including a wavelength optimized for a fluorescent material labeled to a sample, a wavelength which parameterizes a detectable fluorescence intensity greater than 75% and less than 100% of a fluorescence intensity detected with the optimum wavelength, a wavelength which parameterizes a detectable fluorescence intensity greater than 50% and less than 75% of the optimum wavelength fluorescence intensity, a wavelength which parameterizes a detectable fluorescence intensity greater than 25% and less than 50% of the fluorescence intensity parameterized by the optimum wavelength and a wavelength which parameterizes a detectable fluorescence intensity greater than 0% and less than 25% of the fluorescence intensity parameterized by the optimum wavelength. More preferably, fluorescence intensities parameterized by as many wavelengths as possible confined in the overall wavelength band the fluorescent material labeled to the sample has may be detected.

Figure 9:
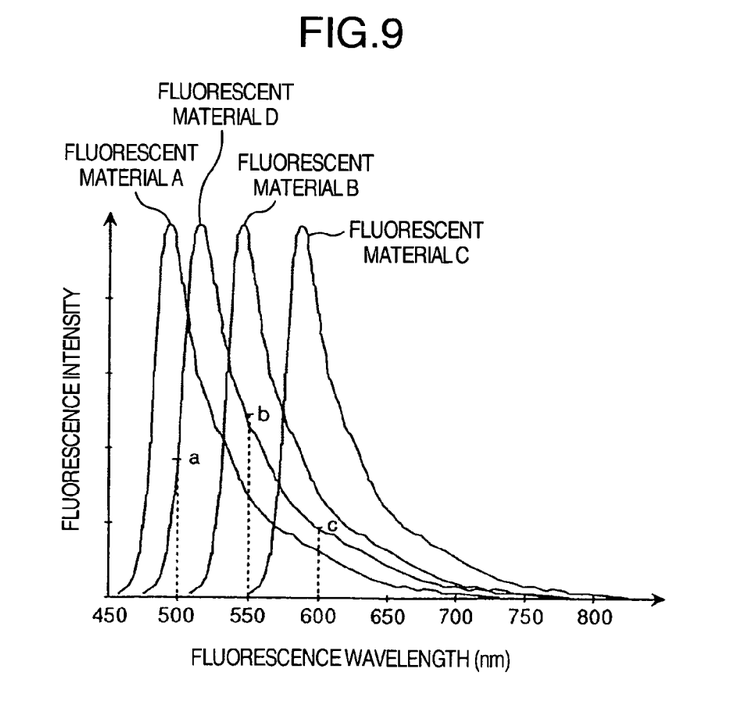
FIG. 9 is a graphical representation showing common fluorescent luminescence spectra having excitation wavelengths at 500 nm, 520 nm, 550 nm and 600 nm, respectively.

In the electrophoresis process or liquid chromatography, a fluorescent material or a sample labeled with the fluorescent material is detected while being separated and in such a case, a plurality of samples labeled with a plurality of different fluorescent materials as shown in FIG. 9 can also be used. In this case, wavelengths as described above are selected in respect of the individual fluorescent materials in order that wavelengths used for detection differ for the plurality of samples labeled with the plural different fluorescent materials and the individual samples can be discriminated from one another. Preferably, in measuring the samples, times to detect different samples will not overlap for the sake of avoiding overlapping of fluorescence intensities.

Further, when performing relative quantitative measurement of concentrations of the plural different fluorescent materials or the samples labeled with the fluorescent materials as shown in FIG. 9 on the basis of a standard sample of known concentration, it is preferable that a fluorescent material labeled to the standard sample will overlap with, even slightly, a detection wavelength optimized for all fluorescent materials labeled to the samples to be inspected. For example, a fluorescent material D in FIG. 9 exhibiting a fluorescence spectrum of 520 nm most overlaps fluorescence spectra of plural different fluorescent materials labeled to samples and therefore this fluorescent material may preferably be used. More preferably, in the example of FIG. 9, a standard sample supposed to be used with the fluorescent material D exhibits fluorescence intensities a, b and c, where a>0, b>0 and c>0, at wavelengths optimized for fluorescent materials A, B and C of inspection samples and then, by marking to the standard sample a fluorescent material having a wavelength range conditioned such that a+b+c is maximized, detection of the plural inspection samples can be assured using as small a number of standard samples as possible. If the standard sample is permitted to be plural in number, a plurality of standard samples labeled with fluorescent materials identical to a plurality of fluorescent materials labeled to inspection samples, respectively, may be prepared to ensure that more preferably, peaks of the standard samples always exhibiting the maximum fluorescence intensity in correspondence with fluorescent materials labeled to the inspection samples can be obtained and the S/N ratio accuracy can be improved.

Figure 1:
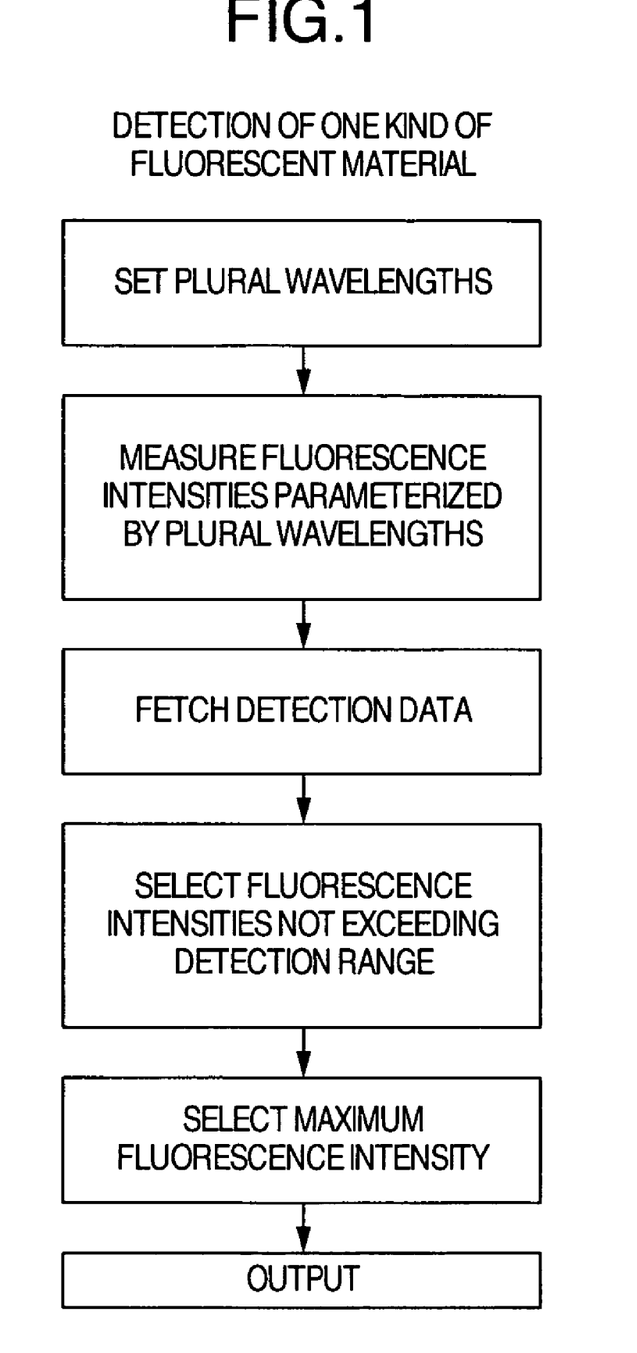
FIG. 1 is a diagram showing a flow of selecting, from a plurality of fluorescence intensities obtained form one kind of fluorescent material, a fluorescence intensity used as an output.
Figure 2:
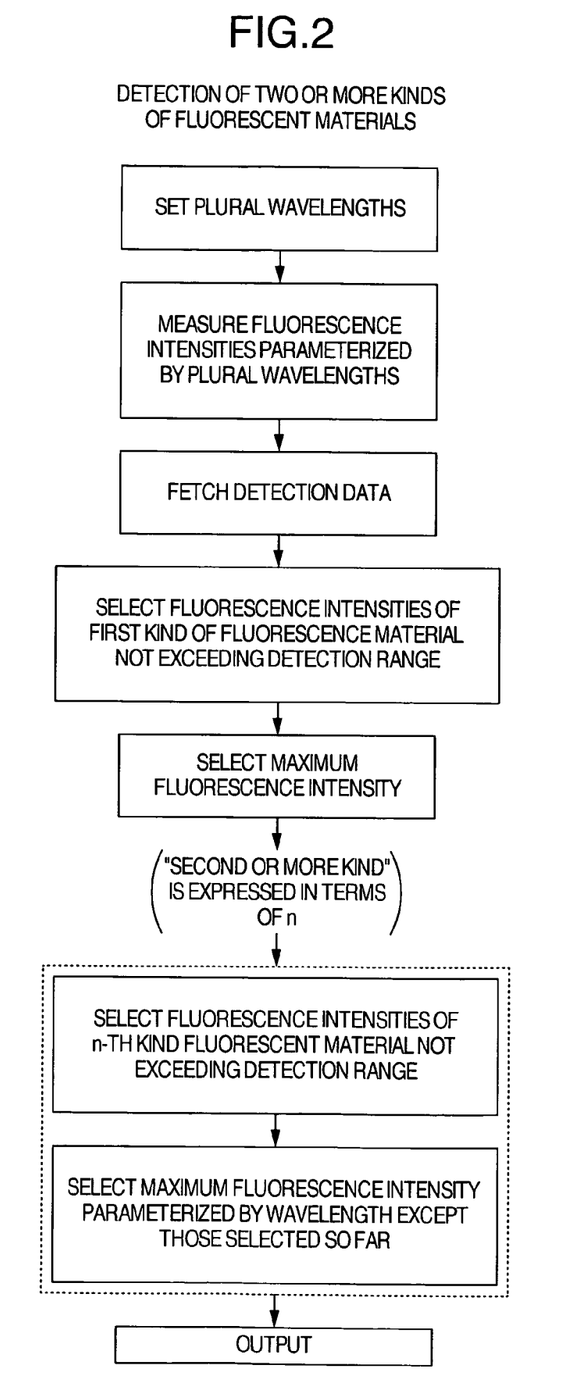
FIG. 2 is a diagram showing a flow of selecting, from a plurality of fluorescence intensities obtained form a plurality of fluorescent materials, a fluorescence intensity used as an output.

Simultaneously obtained detection data of fluorescence intensities parameterized by a plurality of wavelengths according to the aforementioned method are processed in the operation processor (computer) in accordance with the flow shown in FIGS. 1 or 2, and the thus processed detection data of fluorescence intensities are stored in the memory unit and delivered to the output unit as necessary. In FIG. 1, selection of the maximum fluorescence intensity not exceeding the detection range is indicated and normally this is the most rational. But, in some case, a fluorescence intensity associated with or parameterized by a wavelength other than that for the maximum fluorescence intensity can obviously be used. This holds true for FIG. 2.

Prior to describing embodiments of the invention, a description will first be given of figures in the accompanying drawings. FIG. 1 shows a flow of selecting a fluorescence intensity used as a detection result from a plurality of fluorescent intensities parameterized by a plurality of wavelengths and detected from one kind of fluorescent material. A prepared fluorescent material or a sample labeled with the fluorescent material is separated through, for example, electrophoresis process and fluorescent luminescence rays emanated from the fluorescent material are detected sequentially by means of the apparatus shown in FIGS. 3 or 4. In the present invention, even a sample having its concentration unadjusted or a sample having unknown concentration can undergo, as it is, analysis.

The conventional method requires a concentration adjustment based on skilled technique to be made such that the detection result can enter a predetermined detection range of detection intensities parameterized by wavelengths and if the result is outside the detection range, the concentration of a sample must be readjusted. Further, as in the case of the method shown in the aforementioned Patent Document, the sensitivity of the detector must be changed. The most important one of requisites of the present invention is to set in advance a plurality of detection wavelengths in the fluorescence detector, for example, a CCD detector as shown in FIGS. 6, 7, 8A and 10A. Then, fluorescent luminescence rays emanated from a fluorescent material, which are parameterized by the plural preset wavelengths, are detected simultaneously. Through this, even when fluorescence intensities parameterized by 600 nm and 610 nm deviate from the detection range as in the case of, for example, sample A shown in FIG. 6, fluorescence intensities parameterized by wavelengths greater than 650 nm can be obtained at a time as ones not exceeding the detection range. Details in this respect will be described in embodiment 1.

In simultaneously detecting two or more different samples labeled with the same fluorescent material, when the individual samples differ greatly in fluorescence intensity or when the fluorescence intensities of the individual samples mostly overlap with or approach to each other to make discrimination difficult, different fluorescence intensities can be used for detection of the individual samples, so that the S/N ratio of fluorescence intensities the individual samples exhibit can be kept to be high and clear and easy discrimination can be assured. Details to this effect will be described in embodiment 2.

Figure 10A:
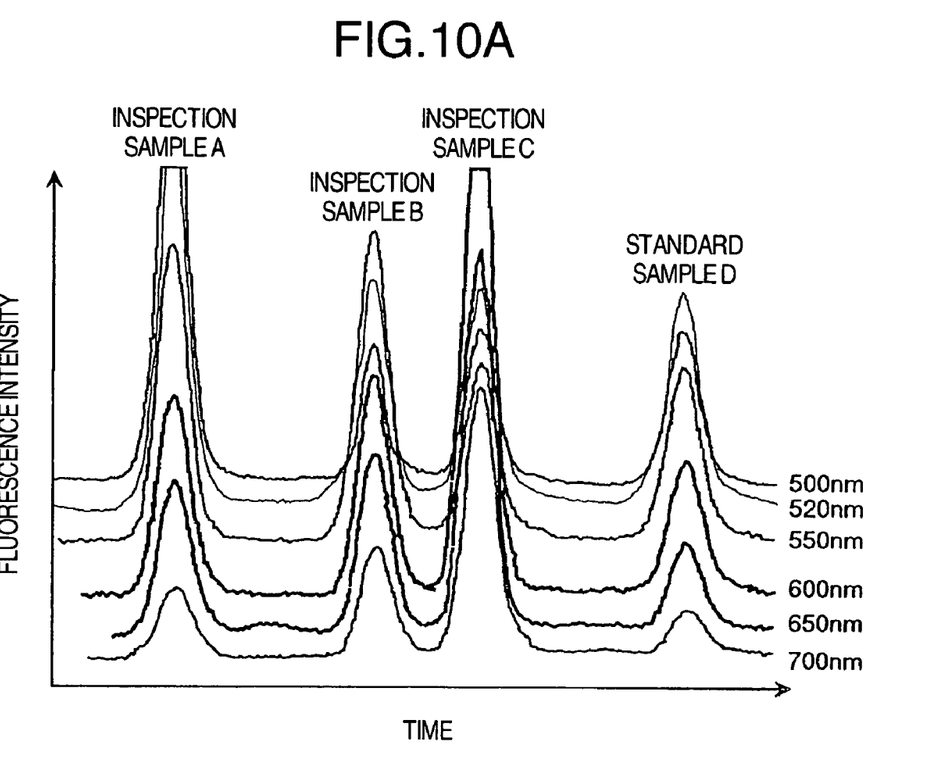
FIG. 10A is a graphical representation showing fluorescence intensity outputs when fluorescence intensities parameterized by a plurality of waveforms three kinds of inspection samples and one kind of standard sample exhibit each are detected in an embodiment of the invention.
Figure 10B:
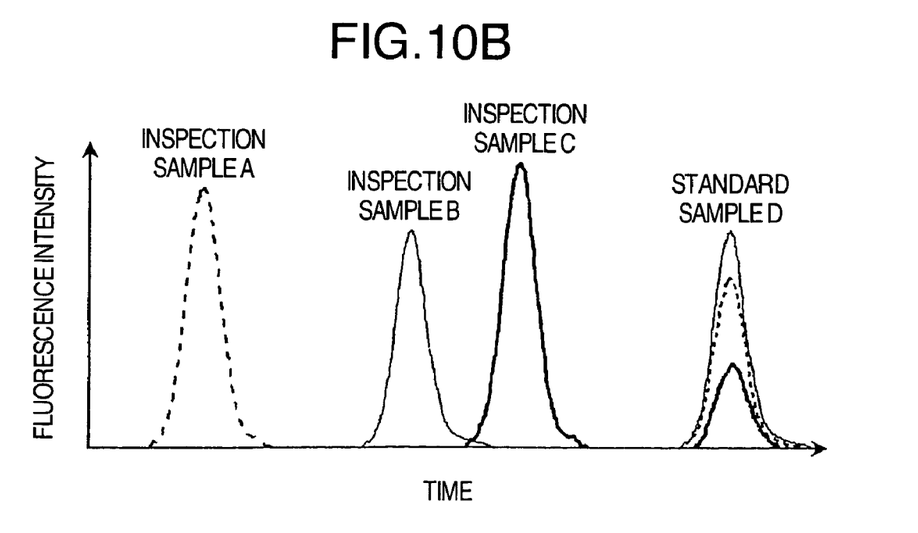
FIG. 10B is a graphical representation showing outputs when three kinds of inspection samples and one kind of standard sample are detected and thereafter only fluorescence intensities parameterized by wavelengths selected for peaks of the individual samples are delivered in an embodiment of the invention.

FIG. 2 shows a flow of selecting, from a plurality of fluorescence intensities, a fluorescence intensity used as a result when, in respect of a plurality of fluorescent materials or samples labeled with the fluorescent materials, the plurality of fluorescence intensities are detected for the individual fluorescent materials. For example, it happens that fluorescence intensities of a plurality of kinds of samples are difficult to discriminate as shown in FIG. 10A and therefore, a method for selecting detection wavelengths in respect of the individual samples as shown in FIG. 10B is employed. Details to this effect will be described in embodiment 3.

FIG. 3 schematically shows the construction of a detection apparatus to which the present invention is applied. As shown, a sample is excited with an exciting light ray from an excitation light source and resulting fluorescent luminescence rays are detected by means of the detector such as a CCD. In this case, the CCD detector is set in advance under the command of a program stored in the memory unit or operation processor so that the detector may make detection of intensities parameterized by a plurality of detection wavelengths. Fluorescence intensities are fetched to the operation processor and caused to undergo a predetermined process so as to be delivered to the output unit. As necessary, the result is stored in the memory unit.

Figure 4A:
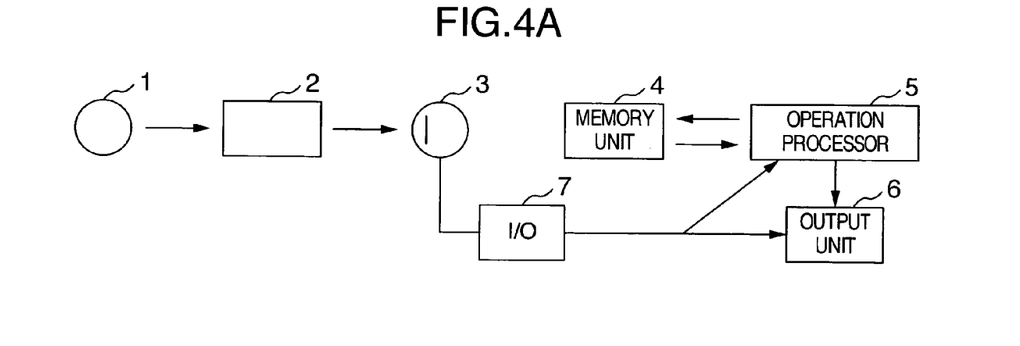
FIGS. 4A and 4B are schematic diagrams useful to explain examples of detection operation with the detection apparatus applied with the invention.
Figure 4B:
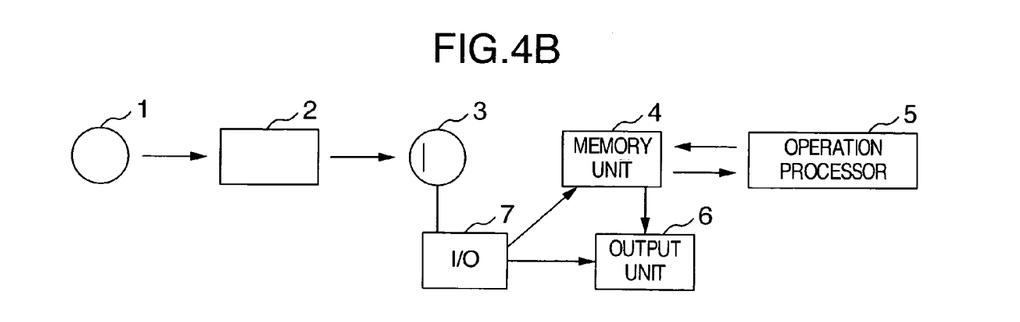

FIGS. 4A and 4B schematically and exemplarily show how the detection apparatus applied with the present invention is configured for detection, where reference numeral 1 designates a light source, 2 a sample, 3 a detector, 4 a memory unit, 5 an operation processor, 6 an output unit and 7 an input/output unit.

FIG. 5 shows a graph of a fluorescence spectrum obtained through conventionally used common detection method in the case of a general fluorescent material having an excitation wavelength at 600 nm.

Figure 6:
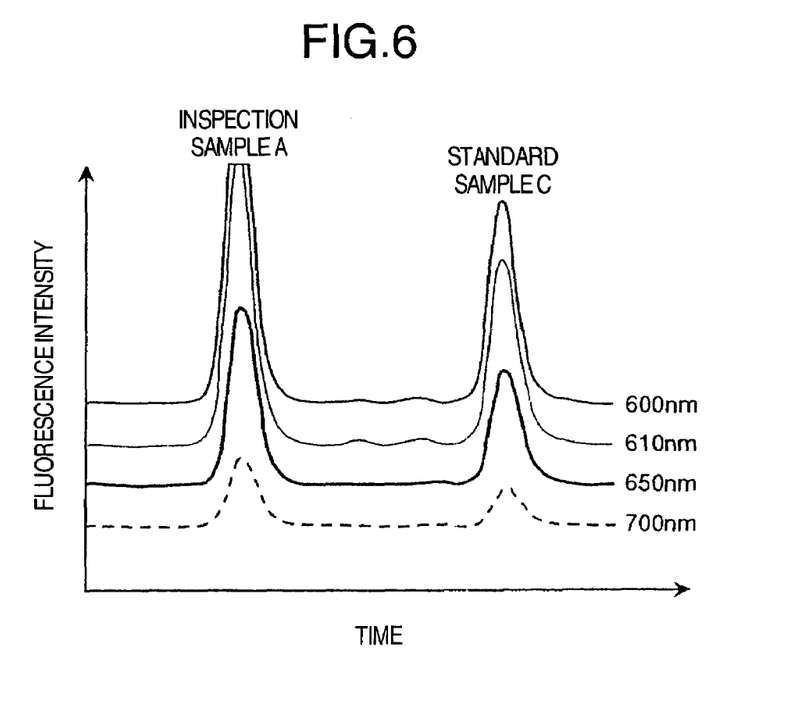
FIG. 6 is a graphical representation of the fluorescence intensity output screen when a plurality of fluorescence intensities are detected simultaneously in an embodiment of the invention, showing a plurality of fluorescence intensity outputs including fluorescence intensities exceeding a detection range.

FIG. 6 shows a graphical representation indicative of the detection screen when a plurality of fluorescence intensities are detected simultaneously in an embodiment of the invention, demonstrating that the plural fluorescence intensities parameterized by a plurality of wavelengths, including those in excess of a detection range, are delivered.

Figure 7:
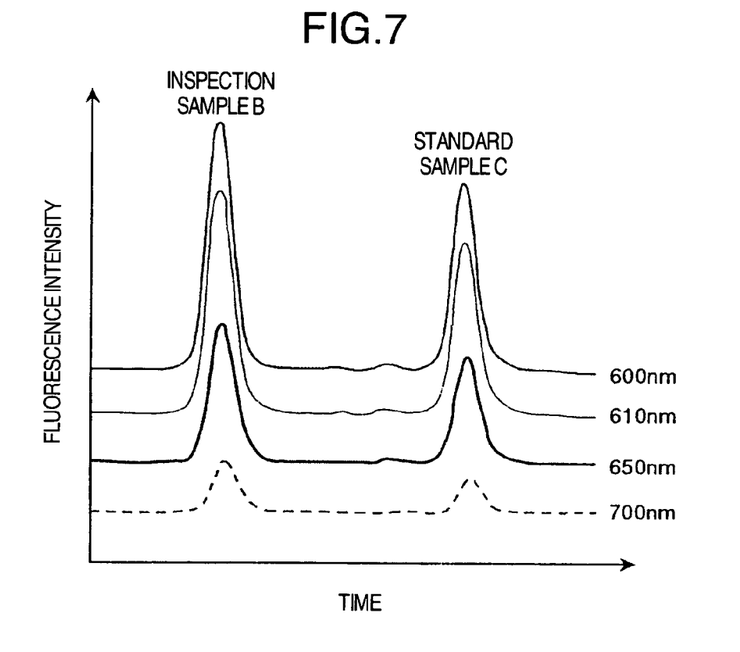
FIG. 7 is a graphical representation of the detection screen when a plurality of fluorescence intensities are detected simultaneously in an embodiment of the invention, showing a plurality of fluorescence intensity outputs exemplifying detection results not exceeding the detection range.

FIG. 7 shows a graphical representation indicative of the detection screen when a plurality of fluorescence intensities are detected simultaneously in an embodiment of the invention, demonstrating an example where all of the plural fluorescence intensities parameterized by a plurality of wavelengths do not exceed the detection range and they are delivered.

Figure 8A:
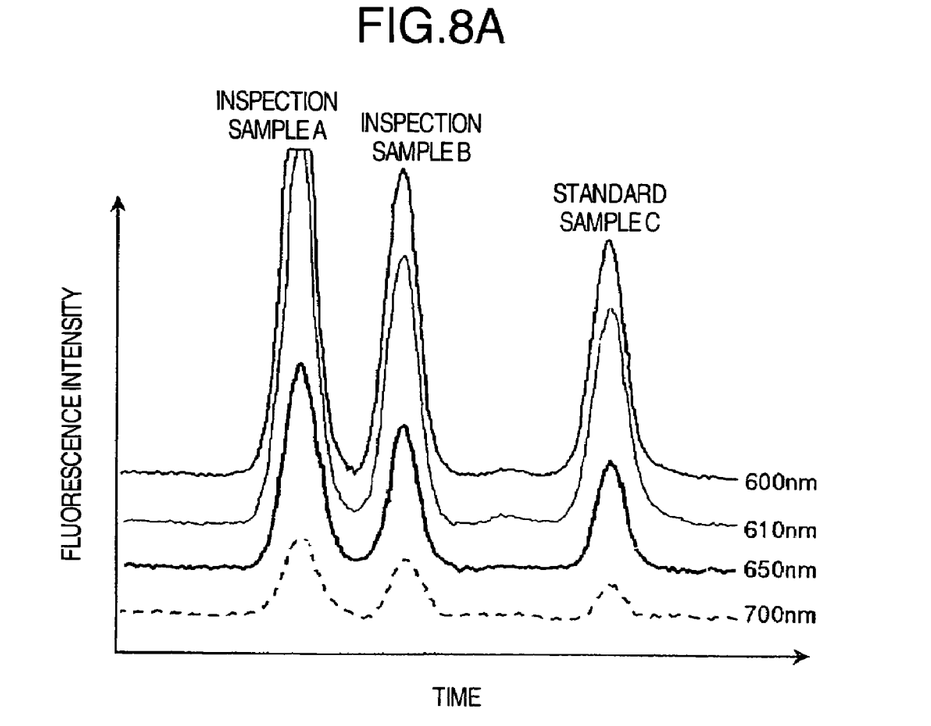
FIG. 8A is a graphical representation showing fluorescence intensity outputs when fluorescence intensities three kinds of samples exhibit each are measured simultaneously in an embodiment of the invention.
Figure 8B:
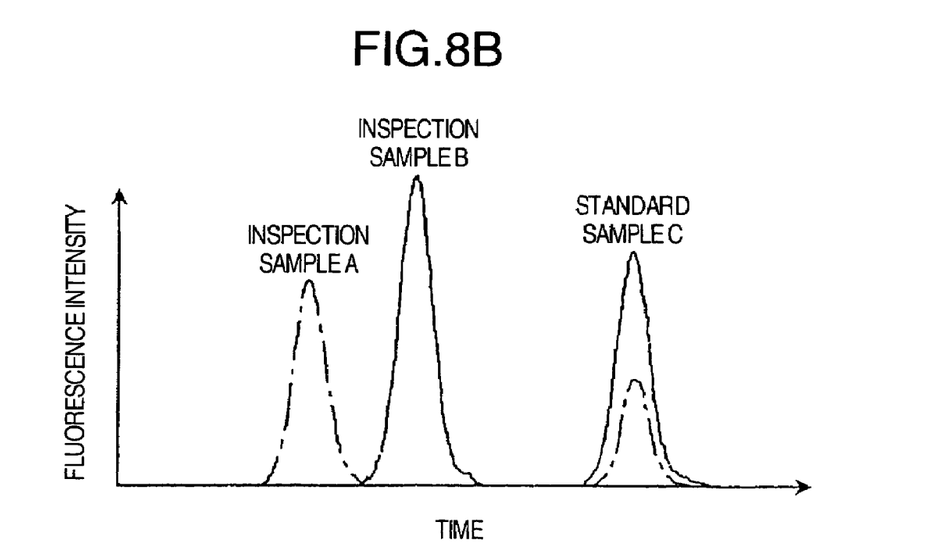
FIG. 8B is a graphical representation showing outputs when two kinds of inspection samples and one kind of standard sample are detected and thereafter only fluorescence intensities parameterized by wavelengths selected for peaks (meaning of which is to be defined in a successive description) of the individual samples are delivered in an embodiment of the invention.

FIG. 8A shows that plural fluorescence intensities parameterized by a plurality of wavelengths are delivered in connection with three kinds of samples when the plural fluorescence intensities of each of the three kinds of samples are measured simultaneously in an embodiment of the invention. FIG. 8B shows that two kinds of inspection samples and one kind of standard sample are detected in an embodiment of the invention and thereafter only fluorescence intensities parameterized by wavelengths selected for peaks of the individual samples are delivered.

FIG. 9 shows a graph of fluorescence spectra obtained by using the conventional, commonly used detection method in respect of common fluorescent materials having excitation wavelengths at 500 nm, 520 nm, 550 nm and 600 nm, respectively.

FIG. 10A shows that fluorescence intensities parameterized by a plurality of wavelengths are delivered when three kinds of inspection samples and one kind of standard sample are detected in an embodiment of the invention. FIG. 10B shows that intensities, parameterized by a plurality of wavelengths, of three kinds of samples and one kind of standard sample are detected and thereafter only fluorescence intensities parameterized by wavelengths selected for peaks of the individual samples are delivered as results.

FIG. 11 shows a fluorescence picture image according to the aforementioned Patent Document disclosing the conventional technique, depicting a fluorescence intensity output when the sensitivity of the amplifier is changed.

The present invention will now be described in greater detail by way of embodiments thereof but the following embodiments are for illustration purpose only and it should be understood that used wavelengths, the kind of fluorescent materials, detection wavelength range, spectrum indication method and method for quantitatively determining concentration from detected intensities parameterized by wavelengths are in no way limitative.

Embodiment 1

The present embodiment is directed to concentration detection of an analytical sample. The present embodiment will be described specifically with reference to the accompanying drawings by taking a case in which nucleic acid labeled with a fluorescent material having an optimum excitation wavelength at 600 nm is detected quantitatively, for instance, but the present invention is not limited to the following concrete example, inasmuch as plural fluorescent luminescence rays from the fluorescent material may be detected simultaneously and fluorescence intensities within the detection range may be determined as detection results.

1. Sample Preparation

Inspection samples A and B of unknown concentration each labeled with a fluorescent material having an excitation wavelength at 600 nm and a standard sample C labeled with the fluorescent material and having a concentration of 20 ng/μl are prepared. Then, the inspection sample A and standard sample C are mixed together by an equal quantity to form a measuring sample AC and the inspection sample B and standard sample C are mixed together by an equal quantity to form a measuring sample BC. The fluorescent material having the 600 nm excitation wavelength exhibits a fluorescent luminescence spectrum as shown in FIG. 5. Having FIG. 5 in mind, waveforms detectable by the CCD detector are set to four wavelengths of 600 nm, 610 nm, 650 nm and 700 nm and the following experiment is made.

2. Simultaneous Detection of Fluorescent Luminescence Rays Associated with Plural Wavelengths While subjecting the measuring sample AC and measuring sample BC to electrophoresis so as to separate them, an exiting light ray is irradiated on them so that fluorescence intensities parameterized by four wavelengths of 600 nm, 610 nm, 650 nm and 700 nm may be measured simultaneously by means of the CCD detector and as a result, changes with time of fluorescence intensities parameterized by the individual wavelengths as shown in FIG. 6 are obtained in respect of the measuring sample AC and changes with time of fluorescence intensities parameterized by the individual wavelengths as shown in FIG. 7 are obtained in respect of the measuring sample BC.

3. Selection of Detection Data

In the case of plural fluorescence intensities of the measuring sample AC (FIG. 6), detected peaks of detection sample A parameterized by the same wavelengths 600 nm and 610 nm as those shown in FIG. 7 (hereinafter, in the specification, a waveform signifying the existence of a fluorescence intensity obtained in relation to time axis, where time is plotted on X axis and fluorescence intensity is plotted on Y axis, is defined as a peak) have flattened tops, exceeding the detection range, and therefore a fluorescence intensity parameterized by 650 nm is selected. On the other hand, in the case of the measuring ample BC, even an intensity parameterized by optimum detection wavelength 600 nm does not exceed the detection range (FIG. 7) and therefore the fluorescence intensity parameterized by 600 nm is selected. The selected fluorescence intensities of peaks of the individual samples are converted in terms of the concentration of the standard sample C, thereby ensuring that the concentration of inspection sample A in the measuring sample AC and the concentration of inspection sample B in the measuring sample BC are calculated in accordance with a method pursuant to equation (1) to obtain calculation results as shown in Table 1.

(Concentration of inspection sample) =(Fluorescence intensity of inspection sample)×(Concentration of standard sample)/(Fluorescence intensity of standard sample) (1)

TABLE 1

Fluorescence intensities parameterized by detection wavelengths of individual samples and concentrations in measuring samples

|  | Inspection sample A | Standard sample C | Inspection sample B | Standard sample C |
|---|---|---|---|---|
| Detection wavelength (nm) | 650 | 650 | 600 | 600 |
| Fluorescence intensity | 11044 | 7081 | 17122 | 14080 |
| Concentration (ng/μl) | 15.6 | 10 | 12.2 | 10 |

Even in the sample undetectable because its intensity parameterized by the wavelength optimized for the fluorescent material exceeds the detection range as exemplified in the use of the fluorescent material of 600 nm, that sample can be detected without readjusting its concentration, inasmuch as intensities parameterized by the plural different wavelengths are detected simultaneously.

While in the present embodiment the fluorescence intensity of fluorescent luminescence ray is used for concentration measurement, the peak area of the sample may obviously be used.

Embodiment 2

The present embodiment is directed to concentration detection of analytical samples. The present embodiment will be described specifically with reference to the accompanying drawings by taking an instance where nucleic acid is labeled with a fluorescent material having an optimum excitation wavelength at 600 nm but it should be understood that the present invention is not limited to the following concrete example, inasmuch as plural fluorescent luminescence rays from the fluorescent material are detected simultaneously and a fluorescence intensity within a detection range is used to provide a detection result.

1. Sample Preparation

Different inspection samples A and B of unknown concentration and each labeled with a fluorescent material having an excitation wavelength at 600 nm and a standard sample C having a concentration of 30 ng/μl and labeled with the fluorescent material are prepared. Then, the inspection samples A and B and the standard sample C are mixed together by the same amount to form a measuring sample ABC. The fluorescent material having the excitation wavelength at 600 nm exhibits a fluorescent luminescence spectrum as shown in FIG. 5. Having FIG. 5 in mind, wavelengths detectable with the CCD detector are set to four wavelengths 600 nm, 610 nm, 650 nm and 700 nm and the following experiment is carried out.

2. Simultaneous Detection of Fluorescent Luminescence Rays Associated with Plural Wavelengths While subjecting the measuring sample ABC to electrophoresis to separate it, an exciting light ray is irradiated on the sample, fluorescence intensities parameterized by the four wavelengths of 600 nm, 610 nm, 650 nm and 700 nm are measured simultaneously by using the CCD detector and changes with time of the fluorescence intensities parameterized by the individual wavelengths are obtained as shown in FIG. 8A.

3. Selection of Detection Data

In the plural fluorescence intensities obtained through the measurement of the measuring sample ABC, peaks of inspection sample A exhibiting detected intensities parameterized by 600 nm and 610 nm has the flattened top as shown in FIG. 8A, exceeding the detection range and therefore, fluorescence intensities parameterized by 650 nm are selected in respect of the samples A, B and C and the selected fluorescence intensities of the peaks of the individual samples are detected. Then, concentrations of the inspection samples A and B converted in terms of the concentration of standard sample C are calculated by using the method pursuant to equation (1) and results are shown in Table 2.

TABLE 2

Fluorescence intensities parameterized by detection wavelengths of individual samples and concentrations in measuring samples

|  | Inspection sample A | Inspection sample B | Standard sample C |
|---|---|---|---|
| Detection wavelength (nm) | 650 | 650 | 650 |
| Fluorescence intensity | 11044 | 8611 | 7081 |
| Concentration (ng/μl) | 15.6 | 12.2 | 10 |

In simultaneously detecting intensities parameterized by identical wavelengths in respect of the individual different inspection samples A and B and the standard sample C, it will happens as shown in FIG. 58A that the fluorescence intensities of the inspection samples A and B mostly overlap with each other or approach to each other, making discrimination difficult or as in the case of inspection sample B, the peak exhibits low levels of simultaneously detected fluorescence intensities and the S/N ratio accuracy is degraded. In such an event, the intensity parameterized by 650 nm can be detected for inspection sample A and the intensity parameterized by 600 nm can be detected for the inspection sample B in order that fluorescence intensities distinctively different for these samples can be used as detection results, with the result that the S/N ratio accuracy can be increased and the two fluorescence intensities can be discriminated clearly from each other with ease as shown in FIG. 8B.

In the instance as above, for the standard sample C, fluorescence intensities parameterized by the wavelengths used for detection of the individual inspection samples are adopted. More specifically, in the standard sample C adapted for the inspection sample A, a fluorescence intensity parameterized by the 650 nm wavelength is selected and in the standard sample C adapted for the inspection sample B, a fluorescence intensity parameterized by 600 nm wavelength is selected and the selected fluorescence intensities of the peaks of the individual samples are detected. Then, the method pursuant to equation (1) is used to convert the detected fluorescence intensities in terms of the concentration of the standard sample C and calculate concentrations of the inspection samples A and B, obtaining results as shown in Table 3.

TABLE 3

Fluorescence intensities parameterized by detection wavelengths of individual samples and concentrations in measuring samples

|  | Inspection sample A | Standard sample C | Inspection sample B | Standard sample C |
|---|---|---|---|---|
| Detection wavelength (nm) | 650 | 650 | 600 | 600 |
| Fluorescence intensity | 11044 | 7081 | 17122 | 14080 |
| Concentration (ng/μl) | 15.6 | 10 | 12.2 | 10 |

As demonstrated in Table 3, even when the detected fluorescence intensities parameterized by the 600 nm wavelength are used in contrast to Table 2, the concentrations of the inspection samples remain intact. By making the wavelengths for detection of the respective inspection samples coincident with the wavelength set to the standard sample in this manner, a plurality of samples can be discriminated from one another easily while obtaining the same results of concentrations as those detected from the intensities parameterized by the same wavelength.

Embodiment 3

A concrete example of a method of detecting a plurality of fluorescent materials, based on the method shown in FIG. 2, will be described by taking quantitative detection of nucleic acids of unknown concentration labeled with three kinds of different fluorescent materials, for instance.

1. Sample Preparation

Inspection samples A, B and C of unknown concentration labeled with different fluorescent materials, respectively, are each mixed with a standard sample D having a concentration of 40 ng/µl by an identical amount to form a measuring sample ABCD. The fluorescent materials labeled to the samples A, B, C and D have optimum wavelengths at 500 nm, 550 nm and 600 nm, respectively, as shown in FIG. 9. Having FIG. 9 in mind, wavelengths detectable by the CCD detector are set to six wavelengths of 500 nm, 520 nm, 550 nm, 600 nm, 650 nm and 700 nm and the following experiment is made.

2. Simultaneous Detection of Fluorescent Luminescence Rays Associated with Plural Wavelengths While subjecting the measuring sample ABCD to electrophoresis to separate it, an exciting light ray is irradiated on it and fluorescence intensities of excited fluorescence parameterized by the six wavelengths of 500, 520, 550, 600, 650 and 700 (nm) are measured simultaneously. Consequently, as shown in FIG. 10A, the sample A exhibits peaks of intensities parameterized by the wavelengths 500 nm and 520 nm, deviating from the detection range, and a peak having a fluorescence intensity parameterized by 550 nm and maximum within the detection range is obtained. In the inspection sample B, peaks having intensities parameterized by all detection wavelengths can be detected within the detection range and a peak having the maximum fluorescence intensity parameterized by the wavelength 550 nm can be obtained. In the inspection sample C, a fluorescence intensity parameterized by the wavelength 600 nm deviates from the detection range and a peak having a fluorescence intensity parameterized by 650 nm and maximum within the detection range can be obtained. In the standard sample D, peaks having intensities parameterized by all the detection wavelengths can be obtained within the detection range and a peak having the maximum fluorescence intensity parameterized by the wavelength 520 nm can be obtained.

3. Selection of Detection Data

In the fluorescence intensities obtained through the measurement of the measuring sample ABCD, the top of peaks of the inspection sample A is flattened at fluorescence intensities parameterized by 500 nm and 520 nm as shown in FIG. 10A and the top of a peak of the inspection sample C is flattened at a fluorescence intensity parameterized by 600 nm, thus exceeding the detection range.

Accordingly, in the case of inspection sample A, the fluorescence intensity parameterized by 550 nm excluding the fluorescence intensities parameterized by 500 nm and 520 nm is maximum and is selected. For the standard sample D, the fluorescence intensity parameterized by 550 nm identical to that for the inspection sample A is selected and the selected fluorescence intensities of the peaks of the individual samples are detected. Then, the concentration of inspection sample A is calculated from that of standard sample D by using the method pursuant to equation (1).

Next, the peak of the inspection ample B does not deviate from the detection range at a fluorescence intensity parameterized by the optimum wavelength 550 nm but if the fluorescence intensity parameterized by the same wavelength as that for detection of the inspection sample A is delivered, inspection samples can hardly be discriminated from each other. Accordingly, more preferably, a fluorescence intensity parameterized by 520 nm, which wavelength is effective for giving the maximum sensitivity among wavelengths except for 550 nm, is selected. For the standard sample D, a fluorescence intensity parameterized by 520 nm which is the same as that for the inspection sample B is selected and the selected fluorescence intensities of the peaks of the individual samples are detected. Then, the concentration of inspection sample B is calculated from that of standard sample D by using the method pursuant to equation (1).

The peak of the inspection sample C deviates from the detection range at a fluorescence intensity parameterized by the optimum wavelength 600 nm, as described previously. Accordingly, a fluorescence intensity parameterized by 650 nm, which wavelength is effective for giving the maximum detection sensitivity among wavelengths except for 650 nm, is selected. Further, for the standard sample D, a fluorescence intensity parameterized by the same wavelength 650 nm as that for the inspection sample C is selected and the selected fluorescence intensities of the peaks of the individual samples are detected. The concentration of inspection sample C is calculated from that of standard sample D by using the method pursuant to equation (1). The aforementioned fluorescence intensities parameterized by the selected wavelengths the individual samples exhibit are illustrated in image diagram form in FIG. 10B and measured values of the fluorescence intensities the inspection samples A, B and C exhibit and relative concentrations thereof to the concentration of standard sample D are put together in Table 4.

TABLE 4

| | Fluorescence intensities parameterized by detection wavelengths of individual samples and concentrations in measuring samples | | | | | |
| --- | --- | --- | --- | --- | --- | --- |
| | Inspection sample A | Standard sample D | Inspection sample B | Standard sample D | Inspection sample C | Standard sample D |
| Detection wavelength (nm) | 550 | 550 | 520 | 520 | 650 | 650 |
| Fluorescence intensity | 57528 | 37235 | 47311 | 48920 | 63761 | 19014 |

TABLE 4-continued

Fluorescence intensities parameterized by detection wavelengths of individual samples and concentrations in measuring samples

| | Inspection sample A | Standard sample D | Inspection sample B | Standard sample D | Inspection sample C | Standard sample D |
|---|---|---|---|---|---|---|
| Concentration (ng/µl) | 15.45 | 10 | 9.67 | 10 | 33.53 | 10 |

Needless to say, in case all targeted peaks do not deviate from the detection range, fluorescence intensities all parameterized by the same wavelength can be detected but when fluorescence intensities within the detection range, parameterized by the same wavelength, are obtained from the plurality of kinds of fluorescence materials and delivered, there is a possibility that the individual inspection samples are hardly discriminated from one another as described above. This inconvenience can be avoided by selecting different wavelengths for detection as described previously and the plural kinds of fluorescence intensities can be detected clearly distinctively as shown in FIG. 10B.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A fluorescence detection method for irradiating an exciting light ray to a fluorescent material or a sample having the fluorescent material to detect fluorescent rays generated under the irradiation in accordance with a relationship between a time axis and the fluorescent rays, comprising the steps of:
    separating different measuring objects included in the sample, by way of electrophoresis;
    generating fluorescent rays by irradiating said exciting light ray to said fluorescent material or said sample having the fluorescent material;
    simultaneously detecting said fluorescent rays parameterized by a plurality of wavelengths included in a wavelength band of a fluorescent area;
    adopting, from said plurality of wavelengths, wavelengths which parameterize fluorescence intensities detected within a detection range;
    outputting the fluorescence intensities parameterized by said adopted wavelengths as detection results.

2. A fluorescence detection method according to claim 1, wherein at least one adopted wavelength is a wavelength which parameterizes the maximum fluorescence intensity within the detection range.

3. A fluorescence detection method for irradiating an exciting light ray onto a plurality of kinds of fluorescent materials or samples having the fluorescent materials to detect fluorescent rays generated under the irradiation, comprising the steps of:
    simultaneously detecting the fluorescent rays parameterized by a plurality of wavelengths included in wavelength bands of fluorescence areas;
    adopting, from said plurality of wavelengths, wavelengths which parameterize fluorescence intensities detected within a detection range; and
    outputting the fluorescence intensities parameterized by said adopted wavelengths as detection results.

4. A fluorescence detection method according to claim 3, wherein the adopted fluorescence wavelength differs from fluorescence material to fluorescence material.

5. A computer-readable medium having stored thereon instructions which, when executed by a computer, cause the computer to perform the steps of:
    setting a plurality of detection wavelengths to a fluorescence detector;
    irradiating an exciting light ray to a fluorescent material or a sample having the fluorescent material;
    detecting fluorescent rays emitted from the excited fluorescent material;
    deciding whether detected fluorescence spectra include spectra, parameterized by wavelengths, which are outside a detection range; and
    when the spectra parameterized by the wavelengths outside the detection range are included, excluding said wavelengths and using the plural spectra within the detection range or when the spectra parameterized by the wavelengths outside the detection range are not included, using the plural spectra within the detection range.

6. A computer-readable medium, according to claim 5, wherein said fluorescence material is represented by a plurality of kinds of fluorescence materials or said sample having the fluorescence material is represented by a plurality of kinds of samples having said plural fluorescent materials.

* * * * *